United States Patent
Seki et al.

(10) Patent No.: US 6,288,112 B1
(45) Date of Patent: Sep. 11, 2001

(54) USE OF PYRETHROID COMPOUNDS TO PROMOTE HAIR GROWTH

(75) Inventors: Toshihiko Seki, Kanagawa-ken (JP); Seishiro Fujii; Gianpaolo Dotto, both of Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/444,420

(22) Filed: Nov. 19, 1999

Related U.S. Application Data

(60) Provisional application No. 60/109,171, filed on Nov. 20, 1998.

(51) Int. Cl.[7] .................................................. A61K 31/275
(52) U.S. Cl. ........................................... 514/520; 514/880
(58) Field of Search ................................................ 514/520

(56) References Cited

U.S. PATENT DOCUMENTS

| | | |
|---|---|---|
| 3,835,176 | 9/1974 | Matsuo et al. . |
| 4,024,163 | 5/1977 | Elliott et al. . |
| 5,567,704 | 10/1996 | Bianco et al. . |
| 5,807,820 | 9/1998 | Elias . |
| 5,824,686 | 10/1998 | Gormley et al. . |

FOREIGN PATENT DOCUMENTS

| | | |
|---|---|---|
| 0714 601 | 6/1996 | (EP) . |

OTHER PUBLICATIONS

CA125:51524, Miller, T. EP 714601, Jun. 1996.*
Aramburu et al. (1998) *Molecular Cell*, 1:627–637.
Enan et al. (1992) *Biochemical Pharmacology*, 43:1777–1784.
Enz et al. (1997) *Biochemical Pharmacology*, 54:321–323.
Fakata et al. (1998) *Biochemical Pharmacology*, 55:2017–2022.
Iwabuchi et al. (1995) *J. Dermatol. Sci.*, 9:64–69.
Narahashi et al. (1992) *Trends Pharmacol.*, 13:236.
Richter et al. (1995) *Biochemical Pharmacology*, 49:367–373.

* cited by examiner

*Primary Examiner*—Rebecca Cook
(74) *Attorney, Agent, or Firm*—Fish & Richardson P.C.

(57) ABSTRACT

A method of promoting hair growth which includes administering to a subject an effective amount of a pyrethroid. A composition having a pyrethroid and a pharmaceutically acceptable carrier for promoting hair growth is also described.

23 Claims, No Drawings

USE OF PYRETHROID COMPOUNDS TO PROMOTE HAIR GROWTH

This application claims priority to 60/109171 filed Nov. 20, 1998.

BACKGROUND OF THE INVENTION

Unwanted hair loss can plague both men and women of all ages. It can arise as the result of a variety of underlying causes, including hormonal imbalance, genetic redisposition and exposure to toxic substances. Alopecia areata is a non-scarring inflammatory hair loss disease that can affect men, women, and even children. The factors that activate the onset of alopecia and the mechanisms of its development are not well understood. It is characterized clinically by the sudden appearance of a round or oval patch of non-scarring and painless hair loss with spontaneous remissions and exacerbations (Weitzer, *Am. Fam. Physician* 41(4):1197–1201 (1990)). The annual incidence of alopecia areata is approximately 2 per 10,000 population. 5% to 10% of patients, especially children, result in a total loss of all of the scalp hair (alopecia totalis). Although the disease itself is non-life threatening, the cosmetic and psychological impact on both patients and parents is tremendous. Patients usually suffer from a higher than normal rate of major depression and/or other anxiety disorder (Colon et al., *Comprehensive Psychiatry* 32(3): 245–251 (1991); Beard, *J. Am. Acad. Dermatol.* 14(4):697–700 (1986)).

SUMMARY OF THE INVENTION

In general, the invention features, a method of promoting hair growth. The method includes administering to a subject, e.g., a human with an insufficient amount of hair or an insufficient rate of hair growth, an effective amount of a pyrethroid, e.g., a type I pyrethroid or, preferably, a type II pyrethroid, e.g., cypermethrin, deltamethrin, or fenvalerate. In a preferred embodiment, the pyrethroid is administered topically. The pyrethroid can be administered to the scalp, face, chest, legs, and other regions of the body. In a preferred embodiment, the pyrethroid is provided in a composition, e.g., a pharmaceutically acceptable composition. In a preferred embodiment, the weight percent of the pyrethroid ranges from 0.005% to 5%; the weight percent of the pyrethroid ranges from 0.01% to 2%. In a preferred embodiment, the compound is administered at any point in a hair cycle, e.g., in the anagen (growth) phase of hair growth; in the telogen (resting) phase of hair growth; in the catagen (the period between the telogen phase and the anagen phase) phase of hair growth.

In a preferred embodiment, the method includes: identifying a subject in need of hair growth promoting treatment; after administration of a pyrethroid compound, evaluating the effect of the administration on hair growth; the treatment can involve more than one administration, e.g., at least two, three, or four administrations, of the pyrethroid compound.

In a preferred embodiment, the subject can be male or female that suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

In another aspect, the invention features, a method of promoting hair growth. The method includes administering to a subject, e.g., a human with an insufficient amount of hair or an insufficient rate of hair growth, an effective amount of a compound of the formula:

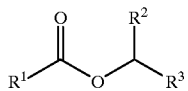

wherein $R^1$ is

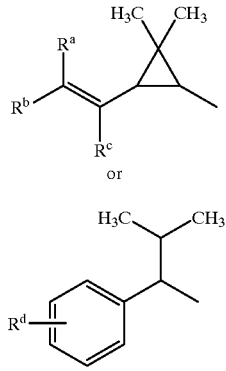

in which each of $R^a$, $R^b$, $R^c$, and $R^d$, independently, is H, fluoro, chloro, bromo, iodo, or $C_{1-4}$ alkyl. Alkyl can be either a straight or branched group. Some examples of alkyl groups are methyl, ethyl, propyl, isopropyl, butyl, isobutyl, and tert-butyl. $R^2$ is CN or C≡CH; and $R^3$ is

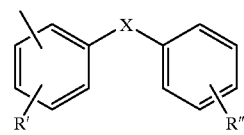

in which X is O, S, NH, or $CH_2$; and each of R' and R", independently, is H, fluoro, chloro, bromo, iodo, or $C_{1-4}$ alkyl. The compound can exist as a salt, e.g., a hydrochloride salt. There can be more than one substituents on each aromatic ring, e.g., more than one $R^d$, R', or R" on each ring.

In a preferred embodiment, the compound is administered topically. The compound can be administered to the scalp, face, chest, legs, and other regions of the body. In a preferred embodiment, the compound is provided in a composition, e.g., a pharmaceutically acceptable composition. In a preferred embodiment, the compound is administered at any point in a hair cycle, e.g., in the anagen (growth) phase of hair growth; in the telogen (resting) phase of hair growth; in the catagen (the period between the telogen phase and the anagen phase) phase of hair growth.

In a preferred embodiment, $R^2$ is CN. In a preferred embodiment, $R^1$ is

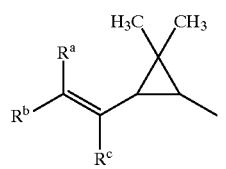

in which each of $R^a$, $R^b$ and $R^c$, independently, is H, fluoro, chloro, bromo, iodo, or $C_{1-4}$ alkyl. In a preferred embodiment, each of $R^a$ and $R^b$, independently, is chloro or bromo; and $R^c$ is H. In a preferred embodiment, each of $R^a$ and $R^b$, independently, is chloro; X is O; and each of R' and R", independently, is H. In a preferred embodiment, each of $R^a$ and $R^b$, independently, is bromo; X is O; and each of R' and R", independently, is H. In a preferred embodiment, $R^1$ is

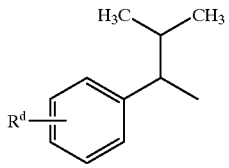

in which $R^d$ is H, fluoro, chloro, bromo, iodo, or $C_{1-4}$ alkyl. In a preferred embodiment, $R^d$ is chloro; X is O; and each of R' and R", independently, is H. In a preferred embodiment, X is O; each of R' and R", independently, is H.

In a preferred embodiment, the method includes: identifying a subject in need of hair growth promoting treatment; after administration of an effective amount of the compound, evaluating the effect of the administration on hair growth; the treatment can involve more than one administration, e.g., at least two, three, or four administrations, of the compound.

In a preferred embodiment, the subject can be male or female that suffers from genetic pattern baldness; suffers from a hormonal disorder which decreases hair growth; has received a treatment, e.g., radiation, or chemotherapy, or a drug which inhibits hair growth; or has had a surgical procedure, e.g., skin graft, which is in need of hair growth.

The invention also includes composition of the compound described herein. Accordingly, in another aspect, the invention features, a composition for promoting hair growth. The preparation can include a pyrethroid, e.g., a type I pyrethroid or, preferably, a type II pyrethroid (e.g., cypermethrin, deltamethrin, or fenvalerate), and a pharmaceutically acceptable carrier. In a preferred embodiment, the composition is sterile. In a preferred embodiment, the composition includes a fragrance. In a preferred embodiment, the weight percent of the pyrethroid in the composition ranges from 0.005% to 5%; the weight percent of the compound in the composition ranges from 0.01% to 2%. In a preferred embodiment, the compound is administered at any point in a hair cycle, e.g., in the anagen (growth) phase of hair growth; in the telogen (resting) phase of hair growth; in the catagen (the period between the telogen phase and the anagen phase) phase of hair growth.

In another aspect, the invention features, a kit for promoting hair growth. The kit includes, a compound described herein and instruction for use of the compound to promote hair growth.

In another aspect, the invention features, a container which includes a compound described herein, wherein the container has one ore more of the following properties: it contains less than 5.0, 1.0, 0.5, or 0.1 g of the compound described herein; it is air tight; it is waterproof; or in addition to the compound described herein, it contains a fragrance or other cosmetic ingredient.

By promoting hair growth is meant an increase in the total mass of hair or the total length of the hairs, in a unit area, e.g., per $cm^2$, as compared to nontreated tissue. It can include one or more of: an increase in the length or growth rate of a hair shaft, an increase in the number of hairs, or an increase in the thickness of a hair. In a preferred embodiment, the growth rate is increased.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications mentioned herein are incorporated by reference in their entirety. In case of conflict, the present specification, including definitions, will control. In addition, the materials, methods, and examples are illustrative only and not intended to be limiting.

Other features or advantages of the present invention will be apparent from the following detailed description of several embodiments, and also from the appending claims.

DETAILED DESCRIPTION

Methods of the invention relate to a composition for promoting hair growth which contains a pyrethroid compound, e.g., a type I or type II pyrethroid compound, as an active ingredient. Preferred compounds are type II compounds. Type I pyrethroid compounds (e.g., permethrin) differ from type II pyrethroid compounds (e.g., cypermethrin) in that type II compounds possess a cyano group on the α-carbon atom of the phenoxybenzyl moiety. Some examples of type II pyrethroid compounds present in the composition of this invention are cypermethrin, deltamethrin, and fenvalerate.

Another aspect of this invention features a composition having a compound of formula (I) as an active ingredient.

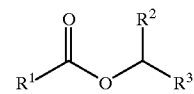

(I)

wherein $R^1$ is

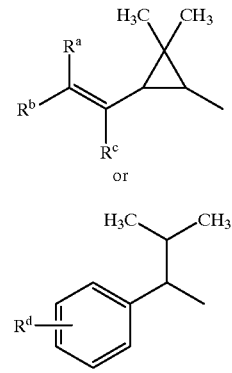

in which each of $R^a$, $R^b$, $R^c$, and $R^d$, independently, is H, fluoro, chloro, bromo, iodo, or $C_{1-4}$ alkyl; $R^2$ is CN or C≡CH; and $R^3$ is

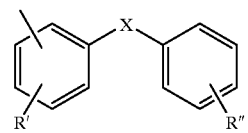

in which X is O, S, NH, or $CH_2$; and each of R' and R", independently, is H, fluoro, chloro, bromo, iodo, or $C_{1-4}$ alkyl. The compounds described above exhibit geometrical and optical isomerism. For example, geometrical isomerism can result from the configuration of different substituents on the cyclopropyl ring with respect to one another and the ring. Optical isomerism can arise from different arrangement of the substituents on the carbon atom attaching to the α-cyano or the α-ethynyl group. Both optically active and racemic mixtures of pyrethroid compounds (or their salts) can be employed in the composition of this invention.

The compounds described above can be synthesized according to procedures known in the art, e.g., by transesterification or Wittig reaction. A detailed description of the preparation of the pyrethroid compounds can be found in U.S. Pat. No. 4,024,163.

A pharmaceutical composition containing a compound described herein in an effective amount can be used to promote hair growth. The compositions can be used to treat alopecia (including androgenic alopecia, e.g., male pattern baldness, and alopecia areata). The use of such a composition for the manufacture of a medicament for promoting hair growth is also within the scope of this invention.

Still another aspect of this invention is a method of promoting hair growth by administering to a subject an effective amount of a compound described herein.

An effective amount of the composition of the present invention is defined as the amount of the composition which, upon administration to an animal in need, confers a hair growth-promoting effect on treated animals. The effective amount to be administered to an animal is typically based on a variety of factors including age, sex, surface area, weight, and conditions of the animal. Body surface area may be approximately determined from height and weight of the patient. See, e.g., Scientific Tables, Geigy Pharmaceuticals, Ardley, N.Y., 1970, 537. An effective amount of a compound described herein in the composition of this invention, i.e., doses, e.g., daily doses, can range from about 0.01 mg/kg to about 25 mg/kg; from about 0.1 mg/kg to about 12.5 mg/kg. Effective doses will also vary, as recognized by those skilled in the art, dependant on route of administration, excipient usage, and the possibility of co-usage with other treatments such as usage of other hair growth-promoting compounds.

The pharmaceutical composition may be administered via the parenteral route, including orally, topically, subcutaneously, intraperitoneally, intramuscularly, intranasally, and intravenously. Topical administration is preferred. Repeated administration of the composition, e.g., repeated topical administration, can be used. More than one route of administration can be used simultaneously, e.g., topical administration in association with oral administration. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the hair growth-promoting composition.

The composition of this invention can also be formulated into dosage forms for other routes of administration utilizing conventional methods. A pharmaceutical composition can be formulated, for example, in dosage forms for oral administration in a capsule, a tablet (each including timed release and sustained release formulations), or a gel seal. Capsules may comprise any standard pharmaceutically acceptable material such as gelatin or cellulose derivatives. Tablets may be formulated in accordance with the conventional procedure by compressing mixtures of pyrethroid compounds and a solid carrier, and a lubricant. Examples of solid carriers include starch and sugar bentonite. The hair growth-promoting composition can also be administered in a form of a hard shell tablet or capsule containing, for example, lactose or mannitol as a binder and a conventional filler and a tableting agent.

Topical administration of the hair growth-promoting compounds described herein presents an attractive route of administration amongst the many different routes described above. Such topical pharmaceutical compositions can exist in many forms, e.g., in the form of a solution, cream, ointment, gel, lotion, shampoo, or aerosol formulation adapted for application to the skin. The weight percent of the active ingredient in the composition, i.e., the pyrethroid compound, useful in promoting hair growth ranges from 0.01% to 5% (based on the total weight of the composition) in admixture with a pharmaceutically acceptable carrier. A wide variety of carrier materials can be employed in the hair growth-promoting composition of this invention such as alcohols, aloe vera gel, allantoin, glycerine, vitamin A and E oils, mineral oils, and polyethylene glycols. Other additives, e.g., fragrance or other cosmetic ingredients, can be present in the composition.

The following specific examples, which describe the hair growth-compositions of this invention and biological testings of such compositions, are to be construed as merely illustrative, and not limitative of the remainder of the disclosure in any way whatsoever.

EXAMPLE 1

The following example was performed to determine if pyrethroid compounds cause skin irritation (as indicated by ear thickness in mice). Skin irritants may contribute to promoting hair growth.

Prior to the experiment, ear thickness of mice (C3H strain, female, 16 weeks of age, n=3/group) was measured with a thickness gage (Mitsutoyo Corp.). After measuring ear thickness of both ears, 10 μL of ethanol was applied on left ear and 10 μL of a pyrethroid solution (1% pyrethroid compound in ethanol) was applied to the right ear. Ear thickness was measured for three consecutive days after administration. The results of left and right ear thickness are tabulated in Table 1 below:

TABLE 1

| | day | | | |
|---|---|---|---|---|
| | 0 | 1 | 2 | 3 |
| | Left Ear | | | |
| Group I | | | | |
| Ethanol only (× 0.01 mm) | 27.7 | 27.7 | 27.3 | 27.7 |
| SD | 0.58 | 0.58 | 0.58 | 1.15 |
| Group II | | | | |
| Ethanol only (× 0.01 mm) | 27.0 | 27.3 | 27.3 | 27.7 |
| SD | 0 | 0.58 | 0.58 | 0.58 |
| Group III | | | | |
| Ethanol only (× 0.01 mm) | 27.3 | 28.3 | 27.7 | 27.3 |
| SD | 0 | 1.15 | 1.15 | 0.58 |
| Group IV | | | | |
| Ethanol only (× 0.01 mm) | 27.3 | 27.7 | 27.3 | 28.0 |
| SD | 0.58 | 0.58 | 0.58 | 1.00 |

TABLE 1-continued

| | day | | | |
|---|---|---|---|---|
| | 0 | 1 | 2 | 3 |
| Right Ear | | | | |
| Group I | | | | |
| Cypermethrin (× 0.01 mm) | 27.7 | 27.7 | 27.3 | 28.0 |
| SD | 0.58 | 0.58 | 0.58 | 1.00 |
| Group II | | | | |
| Deltamethrin (× 0.01 mm) | 27.0 | 27.3 | 27.3 | 28.0 |
| SD | 0 | 0.58 | 0.58 | 1.00 |
| Group III | | | | |
| Fenvalerate (× 0.01 mm) | 27.3 | 28.0 | 28.0 | 27.0 |
| SD | 0.58 | 1.00 | 1.73 | 1.00 |
| Group IV | | | | |
| Permethrin (× 0.01 mm) | 27.3 | 27.7 | 27.7 | 28.3 |
| SD | 0.58 | 0.58 | 0.58 | 1.15 |

As can be seen from Table 1 above, the pyrethroid-containing compositions, i.e., the compositions containing cypermethrin, deltamethrin, fenvalerate, or permethrin did not increase ear thickness when compared to ethanol. In other words, all four compositions tested did not have primary irritancy at a concentration of 1% in ethanol.

EXAMPLE 2

Another ear thickness experiment was performed. Ear thickness of mice (Sencar strain, female, 10 weeks of age, n =3/group) was measured with a thickness gage (Mitsutoyo Corp.). After measuring the thickness of both ears at the beginning of the experiment, 20 µL of 12-O-tetradecanoyl-phorbol 13-acetate (TPA) at a concentration of $10^{-4}$ M in acetone was applied on both ears, followed by the application of 10 µL of ethanol on the left ears and 10 µL of the four compositions tested in Example 1 on the right ears (at a concentration of 1% of pyrethroid compound in ethanol solution). Again, ear thickness was monitored over three consecutive days following administration of the compositions. The results are provide in Table 2.

TABLE 2

| | day | | | |
|---|---|---|---|---|
| | 0 | 1 | 2 | 3 |
| Left Ear | | | | |
| Group I | | | | |
| Ethanol only (× 0.01 mm) | 24.0 | 27.7 | 28.3 | 28.3 |
| SD | 1.00 | 28.0 | 2.52 | 1.53 |
| Group II | | | | |
| Ethanol only (× 0.01 mm) | 26.0 | 28.0 | 29.0 | 29.0 |
| SD | 2.65 | 0.58 | 2.00 | 1.73 |

TABLE 2-continued

| | day | | | |
|---|---|---|---|---|
| | 0 | 1 | 2 | 3 |
| Group III | | | | |
| Ethanol only (× 0.01 mm) | 24.0 | 27.3 | 29.0 | 28.3 |
| SD | 0 | 1.53 | 1.00 | 0.58 |
| Group IV | | | | |
| Ethanol only (× 0.01 mm) | 23.7 | 29.7 | 27.7 | 28.0 |
| SD | 0.58 | 3.06 | 2.08 | 1.73 |
| Right Ear | | | | |
| Group I | | | | |
| Cypermethrin (× 0.01 mm) | 24.0 | 26.7 | 28.3 | 27.3 |
| SD | 1.00 | 0.58 | 2.31 | 0.58 |
| Group II | | | | |
| Deltamethrin (× 0.01 mm) | 26.0 | 27.3 | 29.0 | 28.0 |
| SD | 2.65 | 0.58 | 2.00 | 1.73 |
| Group III | | | | |
| Fenvalerate (× 0.01 mm) | 24.0 | 26.3 | 26.7 | 26.7 |
| SD | 1.00 | 0.58 | 0.58 | 0.58 |
| Group IV | | | | |
| Permethrin (× 0.01 mm) | 23.3 | 27.3 | 27.0 | 27.7 |
| SD | 0.58 | 1.53 | 0 | 0.58 |

As was seen in Example 1, the compositions tested failed to cause skin irritation, as compared to ethanol.

EXAMPLE 3

This experiment was conducted to test the skin irritancy of the compositions of this invention on hair-growing areas of test subjects, i.e., female mice (10 weeks old) of the C3H strain (n=5/group). After clipping the hair of the back skin of mice with an electric clipper, 5 µL/cm$^2$ of each four composition tested in Examples 1 and 2 (at a concentration of 1% in an ethanol solution) were applied. The application was administered once a day, for 3 consecutive days. Skin irritation was evaluated by unaided visual inspection at the end of the third day. The level of irritation was scored as follows:

−: no irritation
±: weak irritation
+: clear irritation
++: strong irritation

The results are presented in Table 3.

TABLE 3

| | Concentration | after 72 hours |
|---|---|---|
| Group I Cypermethrin | 1% in ethanol | − |
| Group II Deltamethrin | 1% in ethanol | − |
| Group III Fenvalerate | 1% in ethanol | − |
| Group IV Permethrin | 1% in ethanol | − |

Based on the results in Table 3, the four compositions, i.e., the compositions containing cypermethrin, deltamethrin, fenvalerate, and permethrin, all failed to cause skin irritation (redness) with three repeated topical administration to mice skin at a concentration of 1% in ethanol.

EXAMPLE 4

The ability of topical administration of pyrethroid compounds to promote hair growth was assessed in female C3H strain mice (10 weeks old; n=5/group). Hair on the back skin of the mice was clipped carefully with an electric clipper. 5 $\mu$L/cm$^2$ of the five compositions tested in the examples above were applied to the mice daily. The level of hair growth at the applied skin areas were evaluated by unaided visual inspection at the indicated time. Cyclosporin A was used as a control. The results are shown in Table 4.

TABLE 4

|  |  | Day | | | | |
| --- | --- | --- | --- | --- | --- | --- |
|  |  | 7 | 14 | 19 | 29 | 36 |
| Group I |  |  |  |  |  |  |
| Cypermethrin | 1% | 0 | 0 | 2 | 4 | 5 |
| Ethanol |  | 0 | 0 | 0 | 0 | 0 |
| Group II |  |  |  |  |  |  |
| Deltamethrin | 1% | 0 | 0 | 1 | 5 | 5 |
| Ethanol |  | 0 | 0 | 0 | 0 | 0 |
| Group III |  |  |  |  |  |  |
| Fenvalerate | 1% | 0 | 0 | 1 | 4 | 4 |
| Ethanol |  | 0 | 0 | 0 | 0 | 0 |
| Group IV |  |  |  |  |  |  |
| Permethrin | 1% | 0 | 0 | 0 | 0 | 0 |
| Ethanol |  | 0 | 0 | 0 | 0 | 0 |
| Cyclosporin A | 1% | 0 | 5 | 5 | 5 | 5 |
| Ethanol |  | 0 | 0 | 0 | 0 | 0 |

The results showed that the compositions containing cypermethrin, deltamethrin, and fenvalerate were effective in promoting hair growth. New hair growth occurred at areas of the skin where the compositions were applied.

EXAMPLE 5

The experiment described in Example 4 was repeated with a commercially available hair growth-promoting compound (5% minoxidil) as a control. The results are shown in Table 5.

TABLE 5

|  |  | Week | | | | | |
| --- | --- | --- | --- | --- | --- | --- | --- |
|  |  | 1 | 2 | 3 | 4 | 5 | 6 |
| Group I |  |  |  |  |  |  |  |
| Cypermethrin | 1% | 0 | 0 | 5 | 5 | 5 | 5 |
|  | 0.1% | 0 | 0 | 5 | 5 | 5 | 5 |
|  | 0.01% | 0 | 0 | 0 | 0 | 0 | 0 |
| Ethanol |  | 0 | 0 | 0 | 0 | 0 | 0 |
| Group II |  |  |  |  |  |  |  |
| Deltamethrin | 1% | 0 | 2 | 5 | 5 | 5 | 5 |
|  | 0.1% | 0 | 0 | 5 | 5 | 5 | 5 |
|  | 0.01% | 0 | 0 | 1 | 1 | 1 | 3 |
| Ethanol |  | 0 | 0 | 0 | 0 | 1 | 1 |
| Group III |  |  |  |  |  |  |  |
| Fenvalerate | 1% | 0 | 0* | 3* | 5 | 5 | 5 |
|  | 0.1% | 0 | 0 | 5 | 5 | 5 | 5 |

TABLE 5-continued

|  |  | Week | | | | | |
| --- | --- | --- | --- | --- | --- | --- | --- |
|  |  | 1 | 2 | 3 | 4 | 5 | 6 |
|  | 0.01% | 0 | 0 | 0 | 0 | 0 | 0 |
| Ethanol |  | 0 | 0 | 0 | 0 | 0 | 0 |
| Group IV |  |  |  |  |  |  |  |
| Permethrin | 1% | 0 | 0 | 0 | 0 | 0 | 1 |
|  | 0.1% | 0 | 0 | 0 | 0 | 0 | 0 |
|  | 0.01% | 0 | 0 | 0 | 0 | 0 | 0 |
| Ethanol |  | 0 | 0 | 0 | 0 | 0 | 0 |
| Minoxidil | 5% | 0 | 0 | 2 | 3 | 4 | 4 |
| Ethanol |  | 0 | 0 | 0 | 0 | 0 | 0 |

*skin color of 2 out of 5 mice was lightened; no hair growth was observed at the indicated time period The results above showed that the three compositions containing cypermethrin, deltamethrin, and fenvalerate were effective in promoting hair growth at concentrations of 0.1% and 1% in ethanol solutions. New hair growth occurred at areas of the skin where the compositions were applied. Moreover, the hair growth potency was dose dependent.

Other Embodiments

From the above description, one skilled in the art can ascertain the essential characteristics of the present invention, and without departing from the spirit and scope thereof, can make various changes and modifications of the invention to adapt it to various usages and conditions. For example, the hair growth-promoting compositions of the invention can contain two or more pyrethroid compounds. Thus, other embodiments are also within the claims.

What is claimed is:

1. A method of promoting hair growth comprising administering to a subject an effective amount of a pyrethroid.

2. The method of claim 1, wherein the pyrethroid is a type I pyrethroid.

3. The method of claim 1, wherein the pyrethroid is a type II pyrethroid.

4. The method of claim 1, wherein the pyrethroid is cypermethrin, deltamethrin, or fenvalerate.

5. The method of claim 1, wherein the pyrethroid is administered topically.

6. The method of claim 1, wherein the pyrethroid is provided in a sterile composition.

7. The method of claim 6, wherein the weight percent of the pyrethroid ranges from 0.005% to 5%.

8. The method of claim 7, wherein the weight percent of the pyrethroid ranges from 0.01% to 2%.

9. A method of promoting hair growth comprising administering to a subject an effective amount of a compound of the formula:

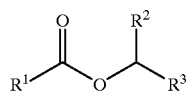

wherein $R^1$ is

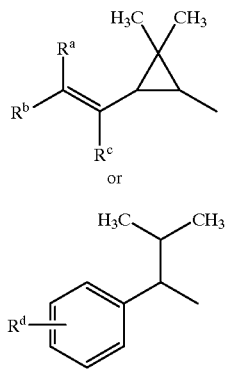

or

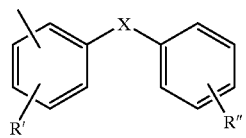

in which each of $R^a$, $R^b$, $R^c$, and $R^d$, independently, is H, fluoro, chloro, bromo, iodo, or $C_{1-4}$ alkyl;

$R^2$ is CN or C≡CH; and $R^3$ is

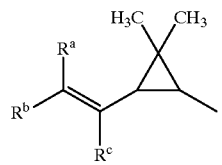

in which X is O, S, NH, or $CH_2$; and each of R' and R", independently, is H, fluoro, chloro, bromo, iodo, or $C_{1-4}$ alkyl;

or a salt thereof.

10. The method of claim 9, wherein said compound is administered topically.

11. The method of claim 9, wherein said compound is provided in a sterile composition.

12. The method of claim 9, wherein $R^2$ is CN.

13. The method of claim 12, wherein $R^1$ is

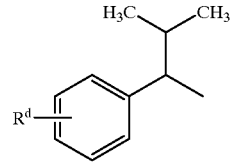

in which each of $R^a$, $R^b$ and $R^c$, independently, is H, fluoro, chloro, bromo, iodo, or $C_{1-4}$ alkyl.

14. The method of claim 13, wherein each of $R^a$ and $R^b$, independently, is chloro or bromo; and $R^c$ is H.

15. The method of claim 14, wherein each of $R^a$ and $R^b$, independently, is chloro.

16. The method of claim 15, wherein X is O; and each of R' and R", independently, is H.

17. The method of claim 14, wherein each of $R^a$ and $R^b$, independently, is bromo.

18. The method of claim 17, wherein X is O; and each of R' and R", independently, is H.

19. The method of claim 12, wherein $R^1$ is

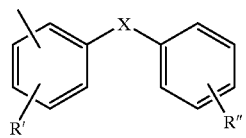

in which $R^d$ is H, fluoro, chloro, bromo, iodo, or $C_{1-4}$ alkyl.

20. The method of claim 19, wherein $R^d$ is chloro.

21. The method of claim 20, wherein X is O; and each of R' and R", independently, is H.

22. The method of claim 12, wherein X is O.

23. The method of claim 22, wherein each of R' and R", independently, is H.

* * * * *